US007541480B2

(12) United States Patent
Bruzzese

(10) Patent No.: US 7,541,480 B2
(45) Date of Patent: Jun. 2, 2009

(54) PROCESS FOR THE PREPARATION OF A COMPOSITION COMPRISING UNSATURATED COMPOUNDS

(75) Inventor: Tiberio Bruzzese, Milan (IT)

(73) Assignee: Pro Aparts-Investimentos E Consultoria LDA, Funchal Madeira (PT)

( * ) Notice: Subject to any disclaimer, the term of this patent is extended or adjusted under 35 U.S.C. 154(b) by 0 days.

(21) Appl. No.: 10/579,331

(22) PCT Filed: Nov. 18, 2004

(86) PCT No.: PCT/EP2004/013115

§ 371 (c)(1),
(2), (4) Date: Dec. 13, 2006

(87) PCT Pub. No.: WO2005/049772

PCT Pub. Date: Jun. 2, 2005

(65) Prior Publication Data

US 2007/0167520 A1 Jul. 19, 2007

(30) Foreign Application Priority Data

Nov. 19, 2003 (IT) .......................... MI2003A2247

(51) Int. Cl.
*C11B 3/00* (2006.01)
*C07C 51/00* (2006.01)

(52) U.S. Cl. .......................... 554/158; 554/175; 554/1; 554/167; 554/186

(58) Field of Classification Search ......... 424/520-525; 554/1, 158, 167, 175, 186
See application file for complete search history.

(56) References Cited

U.S. PATENT DOCUMENTS

| | | | | |
|---|---|---|---|---|
| 4,101,673 | A | 7/1978 | Chang et al. | |
| 4,792,418 | A * | 12/1988 | Rubin et al. | 554/186 |
| 5,023,100 | A | 6/1991 | Chang et al. | |
| 5,855,944 | A | 1/1999 | Koschinski et al. | |
| 6,204,401 | B1 * | 3/2001 | Perrut et al. | 554/205 |

FOREIGN PATENT DOCUMENTS

| | | | |
|---|---|---|---|
| EP | 0255824 | | 2/1988 |
| WO | WO 87/03899 | * | 7/1987 |
| WO | 00/44862 | | 8/2000 |
| WO | 00/71650 | | 11/2000 |

OTHER PUBLICATIONS

Guil-Guerrero et al., "Purification Process for cod Liver Oil Polyunsaturated Fatty Acids", Journal of American Oil Chemists' Society, vol. 78, No. 5, pp. 477-483.*
Council of Europe, Omega-3-acid ethyl esters, 2000, European Pharmacopoeia Commission, European Pharmacopoeia-Supplement 2000, pp. 1008-1011.*
Council of Europe, Quantitative Measurement, 2001, European Pharmacopoeia Commission, European Pharmacopoeia-Supplement 2001, pp. 11-13.*

* cited by examiner

*Primary Examiner*—Porfirio Nazario Gonzalez
*Assistant Examiner*—Yate'k Cutliff
(74) *Attorney, Agent, or Firm*—Oblon, Spivak, McClelland, Maier & Neustadt, P.C.

(57) ABSTRACT

The present invention relates to a process for the preparation of a composition comprising unsaturated compounds, in particular polyunsaturated compounds, which comprises concentrating and purifying the compounds by contact with silicon and/or aluminum derivatives. The process of the invention represents an advantageous substitute of the usual distillation processes, coupled or not to chromatographic processes, and allows to isolate and remove polar byproducts.

10 Claims, No Drawings

PROCESS FOR THE PREPARATION OF A COMPOSITION COMPRISING UNSATURATED COMPOUNDS

The present invention relates to a process for the preparation of a composition comprising unsaturated compounds, in particular polyunsaturated compounds, which comprises concentrating and purifying the compounds.

It is known that unsaturated compounds, in particular the polyunsaturated ones, are scarcely stable and easily deteriorated, amongst others, by atmospheric agents, because of their own reactivity and oxidability on double bonds, with subsequent production of polar oxidation by-products and induction of polymerization.

Among the most instable unsaturated compounds comprised in the composition obtained by the process of the invention, the natural and non-natural oils, of both animal and vegetable origin as well as the products of their chemical modification, like fish and seed oils (triglycerides), the fatty acids and salts thereof obtained by hydrolysis, the alkyl esters thereof obtained by synthesis or by transesterification, as well as any of the derivatives thereof, can be mentioned.

In particular, the family of the compounds deriving from the polyunsaturated fatty acids of the ω-3 series, such as, for instance, the α-linolenic acid (ALA, C18:4 ω-3, all cis), the eicosapentaenoic acid (EPA, C20:5 ω-3, all cis), and the docosahexaenoic acid (DHA, C22:6 ω-3, all cis), and from the polyunsaturated fatty acids of the ω-6 series, as well as the pharmaceutically and dietetically acceptable derivatives thereof, typically the salts and the $C_1$-$C_3$ alkyl esters thereof, can be mentioned.

Among said derivatives, the EPA ethyl ester and/or DHA ethyl ester, alone or in mixture, or even in the presence of other ethyl esters of quantitatively minor ω-3 series compounds, are of particular interest for their use in the pharmaceutical field and as dietetic integrators.

The natural oils containing fatty acids in the form of glycerides are usually submitted to standard treatments, as extraction, whitening, deodorization, etc. The polyunsaturated compounds, as—for instance—the above mentioned acids, being in mixture with high quantities of saturated and monounsaturated components, are usually isolated from glycerides through hydrolysis or through transesterification and concentrated, for instance by complexing the less unsaturated constituents with urea or by other techniques, chemically modified to derivatives, if requested, and then purified by distillation: however, all these steps damage heavily and at the same time the polyunsaturated compound structure and lead to forming high quantities of by-products with polar structure, which sum themselves to the other preexistent impurities of natural oils or deriving by the environmental polluting agents.

Among the instability factors, the atmospheric agents, essentially air oxygen, as well as other oxidizing agents, oxidation catalysts, such as copper and iron; sunlight exposure, hydrolytic agents and the like, can be mentioned. Actually, also many chemical and physical agents, used in the extraction steps of such unsaturated compounds from the natural sources, as well as in the concentration steps and also in the purification steps, can induce some degradation, so forming oxidation and polymerization products. The effect of heating is also particularly dangerous, so that also distillation—while permitting to discard the lower boiling and higher boiling fractions from the oily matrix—induces by itself a high degradation and forming of polymeric residues.

To partially limit such problems, at least in the final steps of the production, molecular distillation is carried out, which is however disadvantageous because of the plant and managing costs and of its limited productivity. In the commercializing steps, storage in tightly closed containers, protected from air and from sunlight, and under inert gas is also adopted. The addition of antioxidants, like for instance tocoferol is also usual.

The polar degradation derivatives are therefore present in the raw materials or are formed in the extraction, concentration, purification steps, as well as during any further step of either chemical or generic manipulation. Among such polar degradation derivatives, most of them having a complex and not completely elucidated structure, we can mention the hydroxy-derivatives on the double bond, the epoxides and peroxides, the last ones being deemed as potentially dangerous to health, in view of their atherogenic and mutagenic activities (see f.i. Carroll K K, Cancer Res. 1975; 35, 3374). Other process by-products are represented by several oligomers and polymers with complex structures, deriving by said double bond oxidation products through different mechanisms involving intermolecular reactions. These polymerization products represent the most abundant by-products and may reach amounts of 20-30% or more.

Completely foreign impurities, of environmental origin, but always present, particularly in fish oils and in all their transformation derivatives, are represented by several toxins, as aflatoxin, hydrocarbons as benzopyrene, pesticides as DDT, industrial agents as PCB and dioxin (McEwen FL, Stephenson GR, The use and significance of pesticides in the environment, Chapter 15. New York, Wiley 1979, 260-348), metallic ions and metallorganic compounds as mercury and methylmercury (Bolger P M, Schwetz B A, N Engl J Med 2002; 347, 1735), and many other marine pollutants, all clearly noxious to health if ingested as food and/or as drug. Other polar derivatives can be constituted by acids deriving from hydrolysis of triglycerides or esters, etc.

To avoid the presence of many foreign substances and by-products in vegetable and animal oils, traditionally used for alimentary purpose, the chemical practice obliged for decades the control of defined parameters as acidity index, peroxide index, iodine index, the search of heavy metals, as mercury and lead and of pesticides, anisidine index, etc.

After the recent development of the derivatives of polyunsaturated fatty acids, more easily oxidized and degraded, as pharmaceutical products, it is now deemed appropriate to carry out a chromatographic analysis determining not only the so-called "gaschromatographic purity", which is indeed an apparent assay (percent ratio of the peak area of each component to the total area of the chromatogram), but even its "true assay" (absolute assay) determined against a pure standard: also the absolute area of the test derivative peak is thus controlled, this technique guaranteeing, in other words, that substantial impurity quantities are not retained in the chromatographic column escaping the instrumental control.

The recent European Pharmacopoeia 2000 (E.P. 2000), in its monograph "Omega-3 acid ethyl esters", a mixture of ethyl esters of omega-3 polyunsaturated acids, typically represented by EPA and DHA, prescribes the direct control of the oxidation and polymerization by-products (defined "oligomers", as a whole, which are not detectable by gaschromatographic route), by means of a specific exclusion chromatography in liquid phase (gel permeation GPC, well known in the art). We will refer hereafter to such specific chromatographic procedures, carried out as described in E.P. 2000.

Coming back to the unsaturated substances object of the process of the invention, just a few of them can be found and extracted from natural products already in high concentration, as oleic acid (monounsaturated) from olive oil; many others are found in low to medium concentration, as arachidonic acid (polyunsaturated, ω-6) in the borage oil, and as EPA and DHA (polyunsaturated, ω-3) in fish oil, where they can be present till to a maximum of 10-20%, as it is easily documented by literature.

The processing of extracted oils (triglycerides) is usually carried out by hydrolysis to acids or by transesterification to esters; acids and esters can be used as such or undergone to chemical modification according to methods known in the art, to give a wide range of derivatives. Frequently, more often during the first steps of the processing, the lower concentrated polyunsaturated substances are partially concentrated f.i. by complexing them with urea and then fractioning/removing the saturated and monounsaturated components, by means of procedures already well-known to the expert by many decades (see Swern D, Techniques of Separation—Urea Mixtures, in "Fatty Acids", part 3, Ed. K S Markley, Interscience, New York, 1963; pages 2309-2358), or even by means of distillation.

Further concentration and final purification are usually carried out by under-vacuum distillation which results to be complicated by severe pyrolytic effects on the unstable unsaturated structures, or by molecular distillation, which limits indeed and yet does not eliminate the thermic degradation and, however, implies expensive plant and managing plant costs and limited productive capacity.

Fractioning with urea and molecular distillation are the techniques, pointed out in the above mentioned monograph, for compositions based on EPA ethyl ester, DHA ethyl ester and other minor components of the ω-3 series. Other occasionally used purification techniques imply the extraction and purification with supercritical fluids, Craig counter current chromatography, and high pressure liquid chromatography (HPLC).

The most relevant patent literature describes what has already been mentioned, as distillation is the final and essential phase to concentration and/or to purification in almost all cases.

For example, U.S. Pat. No. 4,377,526 describes a process for the purification of EPA and the esters thereof, involving the treatment with urea, followed by a fractioned distillation. Percentages of EPA higher than 70% are obtained, while DHA is present at 3-5%.

U.S. Pat. Nos. 4,554,107 and 4,623,488 describe a method based on the technique of molecular distillation: fish oil, enriched in EPA and DHA, with a rather low yield (30%) because of the drastic experimental conditions, is obtained.

U.S. Pat. No. 5,130,061 relates to a process to obtain EPA and DHA as ethyl esters from crude fish oils, through transesterification with ethanol and acid catalyst ($H_2SO_4$), chromatography on silica gel and molecular distillation. Distillation is the essential step of the process, to remove EPA and DHA ethyl esters impurities (concentration 35-40%, Example 3), and to increase their concentration from 40-50% to 80-90% (Examples 4-8) and DHA ethyl ester concentration to 90-96% (Examples 9-10).

Also EP-B-0409903 claims a process, through which oils of animal and/or vegetable origin are undergone to alkaline hydrolysis and the obtained acids are undergone to one or more steps of molecular distillation. The patent points out some prior art processes, based on the use of urea for the precipitation and selective elimination of less unsaturated acids (WO 87/03899, JP 57-187397) or on the extraction with supercritical fluids (JP 60-214757, JP 60-115698).

Further processes of chromatographic type are reported in the following patents: JP 61-291540 uses an absorbent resin composed of a non-polar porous polymer (styrene-divinylbenzene copolymer) and an eluent, containing a hydrophilic polar solvent, preferably methanol, suitably modified, to fraction the required polyunsaturated acid or its ester.

JP 61-037752 uses a chromatographic process on a copolymer, containing monovinyl and polyvinyl aromatic monomers.

JP 58-109444 uses chromatographic columns, composed of a carrier made of silica gel or synthetic polymers (preferably substituted by an octadecyl radical), suitable for a reverse-phase repartition chromatography, and polar eluents, including water, alcohols and other solvents.

Finally, IT 1235879 claims a process, to obtain a particular composition of EPA, DHA and other minor components of ω-3 series, already present in natural fish oil, according to which the known techniques of transesterification, concentration—preferably through a treatment with urea—and molecular distillation are used in free order.

In view of the above prior art, it is believed that the real absolute purity of the obtained products has never been taken into consideration, with the exception of some occasional gaschromatographic data.

For this reason, we believe it is reasonable to think the authors were referring to the simple or apparent gaschromatographic purity, so that—presumably unaware—such processes led to a more far away quality than the supposed one and to products highly contaminated by impurities and polluting agents, and above all, by the already mentioned polar products of degradation (oxidation/polymerization), which are not detectable through gaschromatography, but only through liquid chromatography of exclusion, briefly reported as "oligomers", according to E.P. 2000.

It has been now surprisingly found a process for the preparation of a composition comprising unsaturated compounds with a assay higher than 50% by weight—considered as the absolute assay, according to what above illustrated—, wherein the starting unsaturated compounds are first concentrated up to a gaschromatographic purity corresponding to the assay required for the final unsaturated compounds and then purified by contact with silicon and/or aluminium derivatives.

The process of the invention allows to get purified unsaturated compounds by simply contacting them with silicon and/or aluminium derivatives, without the need of any further manipulation to increase neither the concentration nor the purity of the unsaturated compounds, likely because of the high binding capacity of the polar by-products of the process, of the products of polymerization and of the other impurities/pollutants with the above mentioned silicon and/or aluminium derivatives.

The unsaturated compounds are preferably polyunsaturated compounds; it is also preferred that the composition has a content of oligomeric impurities lower than 30% by weight, in particular lower than 15% by weight.

In the present specification, the expression 'oligomeric impurities' is meant to comprise also other foreign impurities not detectable through gaschromatography.

The polyunsaturated compounds are more preferably long-chain polyunsaturated fatty acids of the ω-3 and/or ω-6 series and/or the pharmaceutically and/or dietetically acceptable derivatives thereof (including the glycerides containing them); in particular, such long-chain polyunsaturated fatty acids contain also monounsaturated and/or saturated compounds.

According to a preferred embodiment, the long-chain polyunsaturated fatty acids of the ω-3 series—comprised in the composition with a assay higher than 50% by weight—are selected from the group consisting of eicosapentaenoic acid (EPA, C20:5 ω-3, all cis) and/or docosahexaenoic acid (DHA, C22:6 ω-3, all cis) and/or the pharmaceutically and/or dietetically acceptable derivatives thereof, whereas the long-chain polyunsaturated fatty acids of the ω-3 series—comprised in the composition with a assay lower than 50% by weight—are selected from the group consisting of C18:3 ω-3 and/or C18:4 ω-3 and/or C20:4 ω-3 and/or C21:5 ω-3 and/or C22:5 ω-3 acids, and/or the pharmaceutically and/or dietetically acceptable derivatives thereof.

The derivatives of the long-chain polyunsaturated fatty acids are preferably selected from the group consisting of the $C_1$-$C_3$ alkyl esters and/or glyceric esters and/or the salts thereof with an inorganic or organic base (sodium, lysine, arginine, choline salts, and the like); the ethyl esters being most preferred.

According to another preferred embodiment, EPA and/or DHA, and/or the derivatives thereof are concentrated up to a gaschromatographic purity higher than 75%, in particular higher than 80%, more preferably higher than 85% and most preferably higher than 90% by weight.

Also variable quantities of ethyl esters of minor ω-3 components, as described in the above-mentioned monograph of E.P. 2000, as well as ω-6, monounsaturated and saturated ethyl esters, usually in quantities even more limited could be present in the composition obtained by carrying out the process of the invention.

In particular, such composition has a content of oligomeric impurities (as well as the other by-products of the process) lower than 2%, more preferably lower than 1.5%, most preferably lower than 1% by weight, according to the analytic specifications required by each commercial products.

Foreign impurities, for example those deriving from environmental pollutants, such as heavy metals, usually measured in concentrations of "parts per million" (ppm), will always be conform to the analytic specifications, in particular the ones of E.P. 2000. A typical composition, obtained by the process of the invention, having an iodine index higher than 320, will have f.i. an acidity index not higher than 2, peroxide index not higher than 20, anisidine index not higher than 20; as well as heavy metals not higher than 10 ppm, Hg and Pb not higher than 1 ppm, pesticides not higher than 2 ppm.

The ratio of EPA to DHA, and/or the derivatives thereof is preferably between 2:1 and 1:2, more preferably between 1.5:1 and 0.9:1.

EPA and/or the derivatives thereof are preferably at least 40% by weight and usually range between 40 and 60% by weight, whereas DHA and/or the derivatives thereof usually range between 25 and 50% by weight and are preferably at least 34% by weight.

According to a further preferred embodiment, the EPA and DHA ethyl esters assay is at least 80% by weight, the EPA ethyl ester assay being at least 40% by weight and the DHA ethyl ester assay being at least 34% by weight; the total ω-3 acids ethyl esters assay being at least 90% by weight. The EPA and DHA ethyl ester assay is preferably higher than 85% by weight.

A still further preferred embodiment of the process of the invention provides that minor ω-3 components, with C20, C21, C22 (or also C18) structure (meaning both acids and/or the derivatives thereof, can be present in a content higher than 1%, preferably higher than 3% by weight, as described in IT 1235879, or be in total (C18:3 ω-3, C18:4 ω-3, C20:4 ω-3, C21:5 ω-3, C22:5 ω-3) about 10%, as reported in the already above mentioned E.P. 2000.

In carrying out the process of the invention, the starting unsaturated compounds may be concentrated by one- or two-step fractioned complexing with urea; further, the resulting concentrated unsaturated compounds being preferably dissolved in aprotic and/or apolar and/or poorly polar solvents before being purified, the solvent being selected, in particular, from the group consisting of n-alkane, iso-alkane or cyclo-alkane. Among the preferred solvents, a $C_5$-$C_8$ alkane such as n-hexane or cyclo-hexane, can be mentioned.

According to a preferred embodiment, the purification is carried out by contacting the concentrated unsaturated compounds with the silicon and/or aluminium derivatives in batch, under stirring; alternatively, the purification is carried out by percolating the concentrated unsaturated compounds through the silicon and/or aluminium derivatives.

The purification is carried out preferably at 10-40° C., in particular at 20-25° C., for a time between 5 minutes to 24 hours, in particular for 0.1-4 hours; further, the purification is advantageously carried out in the dark and in the absence of oxygen.

The silicon and aluminium derivatives preferred for carrying out the process of the invention have, typically, any granulometry, porosity, grade, strength and type and are selected from the group consisting of silica gel; basic, acid or neutral alumina; also their derivatives useful as adsorbents on the basis of bipolar interactions such as, f.i., the silicate, aluminate, and silico-aluminate of such derivatives can be mentioned as well; in particular, the silicon and aluminium derivatives are Florisil® and/or Chromosorbs® and/or Zeolites®.

According to another preferred embodiment, the process of the invention comprises, after the purification, concentrating the resulting unsaturated compounds at a temperature lower than the boiling point of the solvent and at a pressure lower than 200 mm Hg and then evaporating to dryness under vacuum or inert gas flow.

Also preferred is including the composition obtained by the process of the invention in a pharmaceutically and/or dietetically acceptable vehicle and/or excipient and/or diluent; the composition being preferably in the form of soft gel capsules.

The composition obtained by carrying out the process of the invention can be used for the preparation of a pharmaceutical formulation for the prevention and/or treatment and/or prophylaxis of multiple risk factors for cardiovascular diseases, such as hypertriglyceridemia, hypercholesterolemia, and hypertension, and of cardiovascular diseases, such as arrhythmia and atrial and/or ventricular fibrillation, decompensation and cardiac insufficiency; for the primary and secondary prevention of sudden death of cardiac origin and secondary prevention of re-infarction; for the treatment of every other pathology already known as being sensitive to the compositions of EPA and/or DHA or their derivatives, such as autoimmune illnesses, ulcerative cholitis, tumor pathology, nervous system illnesses, cell aging, cerebral infarct, ischemic diseases, psoriasis.

As it is known, the composition can be used to prepare pharmaceutical and/or dietetic formulations suitable for topic, parenteral or oral use, preferably made of soft gel capsules, and contain 250-1500, preferably 300-1000 mg of the composition obtained by carrying out the process of the invention.

Any other known composition comprising unsaturated compounds having a assay higher than 50%, can be obtained, in the above specified limits, by the process of the invention which leads to compounds which can be used for all pharmaceutical and para-pharmaceutical uses (dietetics, etc.) as described in the prior art.

According to the invention, the raw materials have to show a minimum content, measured as gaschromatographic purity, higher than 50% and, in general, equal to the assay required for the finished compound. It will easily be possible to an average man skilled in the art to prepare such raw materials through methods known in literature. For example, a composition of EPA and DHA ethyl esters will easily be obtained through direct transesterification, with ethanol and a catalyst, preferably an alkaline one, of the triglycerides of certain fish oils (sardine, mackerel, codfish, salmon oils, etc.; having, for instance, a content of about 12-18% by weight of EPA and of about 8-12% by weight of DHA), according to known methods (Lehman L W, Gauglitz E J jr., Journal Am. Oil Chem. Soc., 41, 533, 1964).

Starting from such compositions having an overall content of 20-30% by weight of EPA and DHA ethyl esters, it would be easy for an average man skilled in the art to obtain compositions with higher concentration, f.i. higher than 50% by weight, according to methods known in the art (f.i., Abu-Nasr A M et al., Journal Am. Oil Chem. Soc., 31, 16, 1954), f.i. by complexing with urea, followed by isolation and discharging of saturated and monounsaturated components, or by other methods.

In the above mentioned case, by modifying the urea quantities and other experimental parameters, it is possible to reach compositions of EPA and DHA ethyl esters, even higher than 50% or even 75, 80, 85, 90%; all these compositions being useful as raw materials to the purposes of the process of the invention which, as mentioned above, can be carried out even in just one step. Anyway, the compositions having a total concentration of EPA and DHA ethyl esters of 50% by weight, already available on the market, can be, at their turn, concentrated to 75, 80, 85, 90% by weight or more (particularly, when the minor ω-3 components are included), as requested, by means of complexing with urea, wasting saturated and monounsaturated esters, and enrichment of polyunsaturated esters in a further step of preparation.

It is worth noting that the above reported concentrations represent the "apparent assays" of the compositions, which actually—if obtained according to literature procedures, particularly by concentration through urea complexing and if not submitted to additional careful phase of purification—are always undoubtedly contaminated by substantial quantities of "oligomers" as above defined and by other impurities. As mentioned above, the presence of oligomers can be occasionally ranged between 1 and 30%, depending on the process undergone and on the work accuracy: only their presence as well as the apparent assay higher than 50%, involve their use as starting unsaturated compounds in both steps of purification and concentration of the process of the invention. Oligomers in a relatively low range, between 1 and 2%, can therefore characterize both the starting and the final unsaturated compounds, depending on the desired specifications.

In the above mentioned case of compositions based, f.i., on EPA and DHA ethyl esters, the above starting material may be used as such, in oily form, or is preferably dissolved in 3-50 volumes, usually 5-20 volumes, of an aprotic and/or apolar and/or poorly polar solvent, as above mentioned.

According to the process of the invention, the unsaturated compounds are then preferably contacted and/or percolated on inorganic substrates as silicon and aluminium derivatives, so inducing a chemo-physical link with the polar by-products contained, as well as their isolation and removing.

In other words, the capacity to interact and to link (to bind) polar derivatives of unsaturated compounds, particularly oxidation polar derivatives and mainly of oligomeric and polymeric type, with inorganic substrates —typically represented by silicon and aluminium derivatives—allows to obtain a composition which is unexpectedly free of noxious by-products.

The process of the invention is therefore deemed to represent an advantageous substitute of the usual distillation processes, coupled or not to chromatographic processes.

It is also possible to adopt a so-called 'batch process', in this case, preferably under slow stirring, or more preferably by percolation through the silicon or aluminium derivative, with a flow speed depending on the involved volumes, which is not anyway generally critical for the process.

The process of the invention cannot be defined as a 'chromatographic process', because neither fractioning nor discharging of foreign material is requested, since the link of polar and/or oligomeric and/or foreign by-products is strongly selective and specific. In the process of the invention, the solution contacted with the silicon or aluminium derivative can be collected as a unique solution, the gaschromatographic composition remaining substantially unchanged, differently from the distillation processes. This solution is then preferably evaporated to dryness, at a temperature lower than the boiling point of the solvent and at a pressure lower than 200 mm Hg, according to methods known to the average man skilled in the art, and any residual solvent is definitely eliminated, mixing up the oily mass by means of vacuum or inert gas, till a content lower than the one provided in the adopted specifications or fixed by the commercial use or by Pharmacopoeias.

The composition thus obtained has then the absolute purity as requested, it does not need any further purification and can be used as such for all indications and pharmaceutical and para-pharmaceutical formulations known in the prior art.

The composition obtained according to the process of the invention, in particular the composition of EPA and DHA ethyl esters, is therefore conform to the commercial products obtained by molecular distillation and to the products already known for pharmaceutical, para-pharmaceutical, dietetic, alimentary use, etc. as, f.i., the ones described in EP-B-0292846, EP-B-0409903, IT 1235879, EP-B-1152755, partly already mentioned, as well as in the mentioned monograph of E.P. 2000. Therefore, it could be used—for example—in the treatment or the prevention of multiple risk factors for cardiovascular diseases, as disclosed in IT 1235879, in the secondary prevention of cardiovascular events, mortality and sudden death in already infarcted patients, as described in EP-B-1152755, in the prevention and the treatment of other cardiac pathologies, as cardiac insufficiency and decompensation, as reported in EP-A-1365841, as well as in the primary cardiac prevention, in the arrhythmia and atrial and/or ventricular fibrillation treatment, and in all other known therapeutic and non-therapeutic indications, (dietetic, alimentary, etc.).

The following examples illustrate the invention without limiting it.

EXAMPLE 1

15 grams of urea were dissolved in 150 ml of ethanol at 70° C. and under nitrogen. A 10 g composition of EPA and DHA ethyl esters—obtained by transesterification with ethanol and NaOH, followed by a complexing with urea in EtOH/EtOH 95°, according to the disclosure of EP-B-0255824—having 54.2% purity, and 51.0% assay (GC), was added under stirring and far from light. The mixture was kept under stirring for 15 minutes and left to cool. After one night, the precipitate was removed by filtration and the solution was concentrated to a small volume through distillation under a 50 mm Hg pressure. The residue was treated by sodium chloride solution and n-hexane extracted. The organic phase, dried with sodium sulphate and evaporated to dryness, led to a composition of EPA and DHA ethyl esters, 85.6% purity, 77.3% assay (GC).

EXAMPLE 2

5 grams of the composition of EPA and DHA ethyl esters, obtained as per Example 1, were dissolved in 65 ml of hexane and percolated on 6.5 grams of silica gel. The obtained solution was evaporated to dryness at 60° C. and under a 50 mm Hg pressure, working in inert atmosphere far from light. A composition of EPA and DHA ethyl esters was obtained, 85.4% assay (46.6% EPA, 38.8% DHA, GC), acidity index <1, peroxide index <2, heavy metals, Hg, Pb<1 ppm.

EXAMPLE 3

5 grams of a composition of EPA and DHA ethyl esters, 76.5% assay (GC), were treated as per Example 2, through batch procedure and under slight stirring.

In the end, a composition of EPA and DHA ethyl esters was obtained, 82.3% assay (GC), 91.6% total assay of ω-3 ethyl esters, according to the E.P. 2000 specifications.

EXAMPLE 4

5 grams of the composition used in Example 1, were treated as per the procedure of Example 3, finally obtaining a composition with a 53.8% assay (GC).

The invention claimed is:

1. A process for the preparation of a final composition comprising long chain polyunsaturated fatty acids, comprising:

concentrating a composition comprising long chain polyunsaturated fatty acids to a gas chromatographic purity equal to an absolute assay required for a final composition;

dissolving the concentrated composition comprising long chain polyunsaturated fatty acids in at least one solvent selected from the group consisting of an aprotic solvent, an apolar solvent, and a slightly polar solvent; and purifying the dissolved composition comprising long chain polyunsaturated fatty acids by contact with at least one silicon derivative to provide the final composition comprising long chain polyunsaturated fatty acids; wherein the final composition comprising long chain polyunsaturated fatty acids comprises:

one or more compounds having, in total, an absolute assay higher than 50% by weight, selected from the group consisting of eicosapentaenoic acid (EPA, C20:5 ω-3, all cis), docosahexaenoic acid (DHA, C22:6 ω-3, all cis), pharmaceutically acceptable $C_1$-$C_3$ alkyl esters thereof, dietetically acceptable $C_1$-$C_3$ alkyl esters thereof, and salts thereof with an inorganic or organic base; and one or more compounds having, in total, an absolute assay lower than 50% by weight, selected from the group consisting of C18:3 ω-3 acids, C18:4 ω-3 acids, C20:4 ω-3 acids, C21:5 ω-3 acids, C22:5 ω-3 acids, pharmaceutically acceptable $C_1$- $C_3$ alkyl esters thereof, dietetically acceptable $C_1$-$C_3$ alkyl esters thereof, and salts thereof with an inorganic or organic base; and the ratio of EPA to DHA or the $C_1$-$C_3$ alkyl esters or the salts thereof with an inorganic or organic base is between 2:1 and 1:2.

2. The process according to claim 1, wherein the ratio of EPA to DHA, and/or the $C_1$-$C_3$ alkyl esters and/or the salts thereof with an inorganic or organic base is between 1.5:1 and 0.9:1.

3. The process according to claim 1, wherein the EPA and DHA ethyl esters assay is at least 80% by weight, the EPA ethyl ester assay being at least 40% by weight and the DHA ethyl ester assay being at least 34% by weight; the total ω-3, acids ethyl esters assay being at least 90% by weight.

4. The process according to claim 3, wherein the EPA and DHA ethyl ester assay is higher than 85% by weight.

5. The process according to claim 1, wherein the content of the C20, C21 and C22 ω-3 acids and/or $C_1$-$C_3$ alkyl esters and/or the salts thereof with an inorganic or organic base is higher than 1% by weight.

6. The process according to claim 5, wherein the content of the C20, C21 and C22 ω-3 acids and/or $C_1$-$C_3$ alkyl esters and/or the salts thereof with an inorganic or organic base is higher than 3% by weight.

7. A process for the preparation of a composition comprising long chain polyunsaturated fatty acids, wherein the composition comprising long chain polyunsaturated fatty acids comprise one or more compounds having, in total, an absolute assay higher than 50% by weight, selected from the group consisting of eicosapentaenoic acid (EPA, C20:5 ω-3, all cis), docosahexaenoic acid (DHA, C22:6 ω-3, all cis), pharmaceutically acceptable $C_1$-$C_3$ alkyl esters thereof, dietetically acceptable $C_1$-$C_3$ alkyl esters thereof, and salts thereof with an inorganic or organic base; and one or more compounds having, in total, an absolute assay lower than 50% by weight, selected from the group consisting of C18:3 ω-3 acids, C18:4 ω-3 acids, C20:4 ω-3 acids, C21:5 ω-3 acids, C22:5 ω-3 acids, pharmaceutically acceptable $C_1$-$C_3$ alkyl esters thereof, dietetically acceptable $C_1$-$C_3$ alkyl esters thereof, and salts thereof with an inorganic or organic base;

the ratio of EPA to DHA or the $C_1$-$C_3$ alkyl esters or the salts thereof with an inorganic or organic base is between 2:1 and 1:2;

the said long chain polyunsaturated fatty acids are first concentrated up to a gas chromatographic purity corresponding to the assay required for the final composition and then dissolved in aprotic and/or apolar and/or polar solvents before being purified by contact with silicon derivatives, and the purification is carried out in the dark and in the absence of oxygen.

8. A process for the preparation of a composition comprising long chain polyunsaturated fatty acids, wherein the composition comprising long chain polyunsaturated fatty acids comprise one or more compounds having, in total, an absolute assay higher than 50% by weight, selected from the group consisting of eicosapentaenoic acid (EPA, C20:5 ω-3, all cis), docosahexaenoic acid (DHA, C22:6 ω-3, all cis), pharmaceutically acceptable $C_1$-$C_3$ alkyl esters thereof, dietetically acceptable $C_1$-$C_3$ alkyl esters thereof, and salts thereof with an inorganic or organic base; and one or more compounds having, in total, an absolute assay lower than 50% by weight, selected from the group consisting of C18:3 ω-3 acids, C18:4 ω-3 acids, C20:4 ω-3 acids, C21:5 ω-3 acids, C22:5 ω-3 acids, pharmaceutically acceptable $C_{1-C3}$ alkyl esters thereof, dietetically acceptable $C_1$-$C_3$ alkyl esters thereof, and salts thereof with an inorganic or organic base;

the ratio of EPA to DHA or the $C_1$-$C_3$ alkyl esters or the salts thereof with an inorganic or organic base is between 2:1 and 1:2;

the said long chain polyunsaturated fatty acids are first concentrated up to a gas chromatographic purity corresponding to the assay required for the final composition and then dissolved in aprotic and/or apolar and/or polar solvents before being purified by contact with silicon derivatives, and after the purification, concentrating the resulting polyunsaturated compounds at a temperature lower than the boiling point of the solvent and at a pressure lower than 200 mm Hg and then evaporating to dryness under vacuum or inert gas flow.

9. A process for the preparation of a composition comprising long chain polyunsaturated fatty acids, wherein the long chain polyunsaturated fatty acids comprise one or more compounds having, in total, an assay higher than 50% by weight, selected from the group consisting of ω-3 series long chain polyunsaturated fatty acids, ω-6 series long chain polyunsaturated fatty acids, pharmaceutically acceptable $C_1$-$C_3$ alkyl esters thereof, dietetically acceptable $C_1$-$C_3$ alkyl esters thereof, and salts thereof with an inorganic or organic base;

the long chain polyunsaturated fatty acids are first concentrated up to a gas chromatographic purity corresponding to an assay required for a final composition and then dissolved in aprotic and/or apolar and/or polar solvents before being purified by contact with silicon derivatives; and the purification is carried out in the dark and in the absence of oxygen.

10. A process for the preparation of a composition comprising long chain polyunsaturated fatty acids, wherein the long chain polyunsaturated fatty acids comprise one or more compounds having, in total, an assay higher than 50% by weight, selected from the group consisting of ω-3 series long chain polyunsaturated fatty acids, ω-6 series long chain polyunsaturated fatty acids, pharmaceutically acceptable $C_1$-$C_3$ alkyl esters thereof, dietetically acceptable $C_1$-$C_3$ alkyl esters thereof, and salts thereof with an inorganic or organic base;

the long chain polyunsaturated fatty acids are first concentrated up to a gas chromatographic purity corresponding to an assay required for a final composition and then dissolved in aprotic and/or apolar and/or polar solvents before being purified by contact with silicon derivatives; and after the purification, concentrating the long chain polyunsaturated fatty acids at a temperature lower than the boiling point of the solvent and at a pressure lower than 200 mm Hg and then evaporating to dryness under vacuum or inert gas flow.

* * * * *